United States Patent
Shin et al.

(10) Patent No.: US 10,485,472 B2
(45) Date of Patent: Nov. 26, 2019

(54) APPARATUS AND METHOD FOR ESTIMATING SKIN CONDITION

(71) Applicant: SAMSUNG ELECTRONICS CO., LTD., Suwon-si (KR)

(72) Inventors: Eui Seok Shin, Yongin-si (KR); June Young Lee, Seongnam-si (KR); Seung Jun Lee, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 355 days.

(21) Appl. No.: 15/388,374

(22) Filed: Dec. 22, 2016

(65) Prior Publication Data

US 2018/0035941 A1 Feb. 8, 2018

(30) Foreign Application Priority Data

Aug. 4, 2016 (KR) .......................... 10-2016-0099646

(51) Int. Cl.
*A61B 5/00* (2006.01)
*A61B 5/103* (2006.01)

(52) U.S. Cl.
CPC ............ *A61B 5/441* (2013.01); *A61B 5/0075* (2013.01); *A61B 5/103* (2013.01); *A61B 5/443* (2013.01); *A61B 5/445* (2013.01); *A61B 5/4875* (2013.01)

(58) Field of Classification Search
CPC ....... A61B 5/441; A61B 5/0075; A61B 5/443; A61B 5/445; A61B 5/4875
See application file for complete search history.

(56) References Cited

U.S. PATENT DOCUMENTS

| | | | |
|---|---|---|---|
| 6,383,767 B1 | 5/2002 | Polak | |
| 6,671,542 B2 | 12/2003 | Rennert et al. | |
| 7,039,446 B2 | 5/2006 | Ruchti et al. | |
| 7,054,674 B2 | 5/2006 | Cane et al. | |
| 7,317,818 B2 | 1/2008 | Lefebvre | |
| 7,964,390 B2 | 6/2011 | Rozakis et al. | |
| 2001/0041829 A1 | 11/2001 | Thennadil et al. | |
| 2003/0040664 A1 | 2/2003 | Thennadil et al. | |
| 2008/0221412 A1* | 9/2008 | Baker ................. | A61B 5/0059 600/310 |
| 2011/0257492 A1 | 10/2011 | Greve et al. | |
| 2013/0066300 A1 | 3/2013 | Rhee et al. | |
| 2015/0301058 A1 | 10/2015 | Schettini et al. | |

* cited by examiner

*Primary Examiner* — Paula J Stice
(74) *Attorney, Agent, or Firm* — Sughrue Mion, PLLC

(57) ABSTRACT

An apparatus for estimating a skin condition includes a data acquirer configured to acquire an optical absorption spectrum of a skin; and a processor configured to determine content of a component in the skin from the optical absorption spectrum and determine a skin condition based on the determined content of the component in the skin.

13 Claims, 13 Drawing Sheets

APPARATUS AND METHOD FOR ESTIMATING SKIN CONDITION

CROSS-REFERENCE TO RELATED APPLICATION(S)

This application claims priority from Korean Patent Application No. 10-2016-0099646, filed on Aug. 4, 2016 in the Korean Intellectual Property Office, the disclosure of which is incorporated herein by reference in its entirety.

BACKGROUND

1. Field

Apparatuses and methods consistent with exemplary embodiments relate to estimating a skin condition.

2. Description of Related Art

The stratum corneum functions as a barrier to protect the internal structures of a human body from external injury, viruses, bacteria, and other antigens. The stratum corneum is the outermost layer of the skin tissue and is composed of corneocytes and lipid surrounding the corneocytes. Keratin protein fiber exists in the corneocytes. In order to maintain the barrier function, the stratum corneum may need to maintain the contents of protein keratin and lipid therein.

In order to identify a condition of the stratum corneum, the keratin protein content and the lipid content in the stratum corneum may be measured. The measurement of the keratin protein content and the lipid content may be used to evaluate the barrier function of the stratum corneum. The measurement of the keratin protein content in the stratum corneum may be used to diagnose skin diseases caused by overgrowth of the stratum corneum or damage in the lipid.

SUMMARY

According to an aspect of an exemplary embodiment, there is provided an apparatus for estimating a skin condition including: a data acquirer configured to acquire an optical absorption spectrum of a skin; and a processor configured to determine content of a component in the skin based on the optical absorption spectrum and determine a skin condition based on the determined content of the component in the skin.

The component in the skin may include at least one of keratin and lipids.

The processor may extract individual component spectrum data from the optical absorption spectrum and determine the content data of the component in the skin by comparing reference spectrum data of the component with the extracted individual component spectrum data.

The processor may extract the individual component spectrum data from the optical absorption spectrum using a regression analysis algorithm.

The processor may determine at least one of a degree of skin aging and a degree of skin damage based on the determined content of the component in the skin and a skin condition estimation model.

The skin condition estimation model may include at least one of a first estimation model, a second estimation model, a third estimation model, and a fourth estimation model, wherein the first estimation model defines a correlation between the degree of skin aging and keratin content in the skin, the second estimation model defines a correlation between the degree of skin aging and lipid content in the skin, a third estimation model defines a correlation between the degree of skin damage and the lipid content, and the fourth estimation model defines a correlation between the degree of skin damage and a ratio between the lipid content and the keratin content.

The processor may determine stratum corneum transepidermal water (TEWL) from the determined skin condition based on a stratum-corneum-TEWL estimation model.

The stratum-corneum-TEWL estimation model may define a correlation between a degree of skin damage and the stratum corneum TEWL.

The apparatus may further include a display configured to display a result of the determination, and a communication interface configured to transmit the determination result to an external device.

The apparatus may further include a spectroscope configured to emit near-infrared light into the skin and generate the optical absorption spectrum through spectroscopy of the near-infrared light reflected or scattered from the skin.

According to an aspect of another exemplary embodiment, there is provided a method for estimating a skin condition including: acquiring an optical absorption spectrum of a skin; determining content of a component in the skin from the optical absorption spectrum; and determining a skin condition based on the determined content of the component in the skin The determining the content data may include extracting individual component spectrum data from the optical absorption spectrum, and calculating the content data of the component in the skin by comparing reference spectrum data of the component with the extracted individual component spectrum data to determine the content of the component in the skin.

The individual component spectrum data may be extracted from the optical absorption spectrum using a regression analysis algorithm.

The determining the skin condition may include determining a degree of skin aging and a degree of skin damage from the determined content of the component in the skin based on a skin condition estimation model.

The determining the skin condition may include determining stratum corneum transepidermal water (TEWL) from the determined skin condition based on a stratum-corneum-TEWL estimation model.

The method may further include displaying a result of the determination.

The acquiring the optical absorption spectrum may include emitting near-infrared light into the skin and generating the optical absorption spectrum through spectroscopy of the near-infrared light reflected or scattered from the skin.

According to an aspect of another exemplary embodiment, there is provided an apparatus for estimating a skin condition including: a data acquirer configured to acquire an optical absorption spectrum of a skin; and a processor configured to determine a degree of skin damage based on an amplitude of a derivative of the optical absorption spectrum.

The processor may calculate the derivative of the optical absorption spectrum using a Norris gap derivative algorithm or a Savitzky-Golay algorithm.

The processor may execute a degree-of-skin-damage estimation model to determine the degree of skin damage based on the amplitude of the derivate of the optical absorption spectrum, and the degree-of-skin-damage estimation model may be generated in advance based on a correlation between a degree of stepwise skin damage and a second order derivative of the optical absorption spectrum.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1:
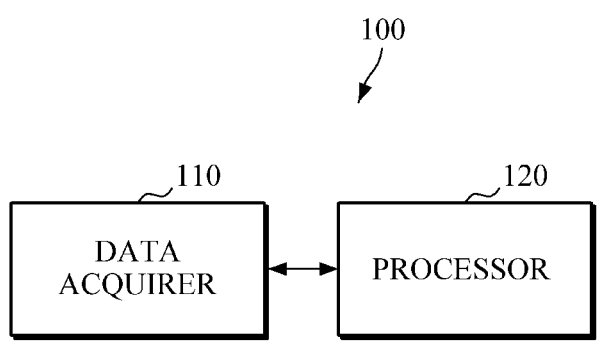
FIG. 1 is a block diagram illustrating an apparatus for estimating a skin condition according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

Expressions such as "at least one of," when preceding a list of elements, modify the entire list of elements and do not modify the individual elements of the list.

FIG. 1 is a block diagram illustrating an apparatus for estimating a skin condition according to an exemplary embodiment. The apparatus 100 may acquire skin spectrum data of a user in a non-invasive manner, extract data of skin components from the skin spectrum data, and estimate the condition of the user's skin based on the extracted data.

The apparatus 100 may be implemented as a software module or manufactured in the form of a hardware chip, and then mounted in an electronic device. In this case, the electronic device may include a mobile phone, a smartphone, a tablet PC, a laptop, a personal digital assistant (PDA), a portable multimedia player (PMA), a navigation system, an MP3 player, a digital camera, and a wearable device, and the wearable device may include devices of a wristwatch type, a wristband type, a ring-type, a belt-type, a necklace type, an ankle band type, a thigh band type, a forearm band type, etc. However, the electronic device is not limited to the above-described examples, nor is the wearable device limited to the above-described examples.

Referring to FIG. 1, the apparatus 100 includes a data acquirer 110 and a processor 120.

The data acquirer 110 may acquire skin spectrum data. Here, the skin spectrum data is optical absorption spectrum data that is acquired by emitting near-infrared light of a predetermined optical wavelength band (e.g., 1500 mn~1900 mn, first overtone band (FOB)) and/or 2000 nm~2400 nm (combination band)) into the user's skin.

According to an exemplary embodiment, the data acquirer 110 may be connected to an external spectroscopy device over a wired/wireless network, and acquire real-time skin spectrum data from the external spectroscopy device, or acquire skin spectrum data received from an external storage device. In that case, the data acquire 110 may be implemented by a communication interface. According to another exemplary embodiment, the data acquirer 110 may be implemented with an spectroscope that includes a light emitter and a light detector (e.g., an optical sensor).

The processor 120 may extract individual component spectrum data from the acquired skin spectrum data. Here, the individual component spectrum data may refer to spectrum data of each component in the skin. For example, the skin components may include water, keratin, lipids, collagen, and the like. Individual component spectrum data, such as a water spectrum, a keratin spectrum, a lipid spectrum, and a collagen spectrum, may be extracted from the acquired skin spectrum data.

According to an exemplary embodiment, the processor 120 may extract the individual component spectrum data from the acquired skin spectrum data using a regression analysis algorithm. Here, the regression analysis algorithm may be a least square regression (LSR) algorithm, a partial least square regression (PLSR) algorithm, a principal components regression (PCR) algorithm, and a multivariate regression algorithm, but the present exemplary embodiment is not limited thereto, such that various algorithms may be used according to an aspect of the acquired skin spectrum data.

The processor 120 may calculate contents of skin components from the extracted individual component spectrum data.

According to an exemplary embodiment, the processor 120 may calculate content data of a component in the skin by comparing the extracted individual component spectrum data with pure spectrum data of the pertinent component. Here, the pure spectrum data may refer to spectrum data of a specific amount of pure component, for example, spectrum data of pure keratin (hereinafter, referred to as pure keratin spectrum data) or spectrum data of pure lipids (hereinafter, referred to as pure lipid spectrum data).

For example, the processor 120 may compare the keratin spectrum data extracted from the skin spectrum data with the pure keratin spectrum data to calculate keratin content data, or may compare the lipid spectrum data extracted from the skin spectrum data with the pure lipid spectrum data to calculate lipid content data.

The processor 120 may estimate the skin condition using the calculated content information about the skin components. Here, the skin condition may include a degree of skin aging and a degree of skin damage.

According to an exemplary embodiment, the processor 120 may estimate a user's degree of skin aging based on a skin condition estimation model (hereinafter, referred to as a "first estimation model") that defines the correlation between the degree of skin aging and keratin content in stratum corneum. For example, the processor 120 may determine the user's degree of skin aging based on keratin content in the stratum corneum of the user's skin and the first estimation model. The processor 120 may input the keratin content to the first estimation model and run the first estimation model to obtain the user's degree of skin aging. In other words, in the case where the first estimation model is built based on the correlation between age and an increase in keratin content, the processor 120 may reference the first estimation model to identify the age that corresponds to the keratin content in the stratum corneum of the user's skin and determine the identified age as the user's skin age, so that the user's degree of skin aging can be estimated.

According to another exemplary embodiment, the processor 120 may estimate the user's degree of skin aging using a skin condition estimation model (hereinafter, referred to as a "second estimation model") which defines the correlation between a degree of skin aging and liquid content in the stratum corneum. For example, the processor 120 may estimate the user's degree of skin aging based on the second estimation model and the lipid content of the stratum corneum of the user's skin. The processor 120 may input the liquid content to the second estimation model and run the second estimation model to obtain the user's degree of skin aging. In other words, in the case in which the second estimation model is built based on the correlation between age and an increase in lipid content, and the processor 120 may reference the second estimation model to identify the age that corresponds to the lipid content in the stratum corneum of the user's skin and determine the identified age as the user's skin age, so that the user's degree of skin aging can be estimated.

According to still another exemplary embodiment, the processor 120 may estimate the user's degree of skin aging using both the first and second estimation models. For example, the processor 120 may estimate the user's degree of skin aging more accurately by combining the degree of skin aging estimated using the calculated keratin content data and the first estimation model and the degree of skin aging estimated using the calculated lipid content data and the second estimation model.

According to yet another exemplary embodiment, the processor 120 may estimate the user's degree of skin damage using a skin condition estimation model (hereinafter, referred to as a "third estimation model") which defines the correlation between a degree of skin damage and lipid content in the stratum corneum. For example, the processor 120 may estimate the user's degree of skin damage based on the third estimation model and the lipid content of the stratum corneum of the user's skin. The processor 120 may input the liquid content to the third estimation model and run the third estimation model to obtain the user's degree of skin damage. In other words, in the case in which the third estimation model is built based on the correlation between a decrease in lipid content and an increase in degree of skin damage, the processor 120 may reference the third estimation model to identify a degree of damage that corresponds to the lipid content of the stratum corneum of the user's skin and determine the identified degree as the user's degree of skin damage, so that the user's degree of skin damage can be estimated.

According another exemplary embodiment, the processor 120 may estimate the user's degree of skin damage using a skin condition estimation model (hereinafter, referred to as a "fourth estimation model") which defines the correlation between a degree of skin damage and a ratio between lipid and keratin in the stratum corneum. For example, the processor 120 may estimate the user's degree of skin damage based on the fourth estimation model and the ratio between lipid and keratin in the stratum corneum. The processor 120 may input the ratio between lipid and keratin to the fourth estimation model and run the fourth estimation model to obtain the user's degree of skin damage. For example, in the case in which the fourth estimation model is built based on a correlation between an increase in skin damage and a decrease in ratio between lipid and keratin, the processor 120 may reference the fourth estimation model to identify a degree of damage that corresponds to the ratio between lipid and keratin in the stratum corneum of the user's skin and determine the identified degree as the user's degree of skin damage, so that the user's degree of skin damage can be estimated.

According to another exemplary embodiment, the processor 120 may estimate the user's degree of skin damage using both the third estimation model and the fourth estimation model. For example, the processor 120 may estimate the user's degree of skin damage more accurately by combining the degree of skin damage which is estimated using the calculated lipid content data and the third estimation model and the degree of skin damage which is estimated using the ratio between lipid and keratin and the fourth estimation model.

The processor 120 may estimate the transepidermal water loss (TEWL) in the stratum corneum from the estimated skin condition. Here, the TEWL in the stratum corneum may refer to the total amount of water lost through the skin.

According to one exemplary embodiment, the processor 120 may estimate stratum corneum TEWL in the user's skin based on a stratum-corneum-TEWL estimation model. Here, the stratum-corneum-TEWL estimation model may be an estimation model which defines the correlation between a degree of skin damage and stratum corneum TEWL. In addition, the stratum-corneum-TEWL estimation model may be generated in advance based on a regression algorithm in which a degree of skin damage is treated as an independent variable and the stratum corneum TEWL and stratum corneum TEWL is treated as a dependent variable.

For example, the processor 120 may estimate the user's stratum corneum TEWL by comparing the stratum-corneum-TEWL estimation model with the estimated degree of skin damage. In other words, in the case in which the stratum-corneum-TEWL estimation model is built based on the correlation between an increase in degree of skin damage and an increase in stratum corneum TEWL, the processor 120 may reference the stratum-corneum-TEWL estimation model to identify stratum corneum TEWL that corresponds to the user's degree of skin damage and determine the identified stratum corneum TEWL as the user's stratum corneum TEWL.

The above-described skin condition estimation models (i.e., the first estimation model, the second estimation model, the third estimation model, and the fourth estimation model) and the stratum-corneum-TEWL estimation model may be generated in advance based on age-, gender-, and disease-specific groups by the processor 120, and may be stored in the apparatus 100 for estimating skin condition or may be received from an external database (DB) through a wired/wireless network.

Figure 2A:
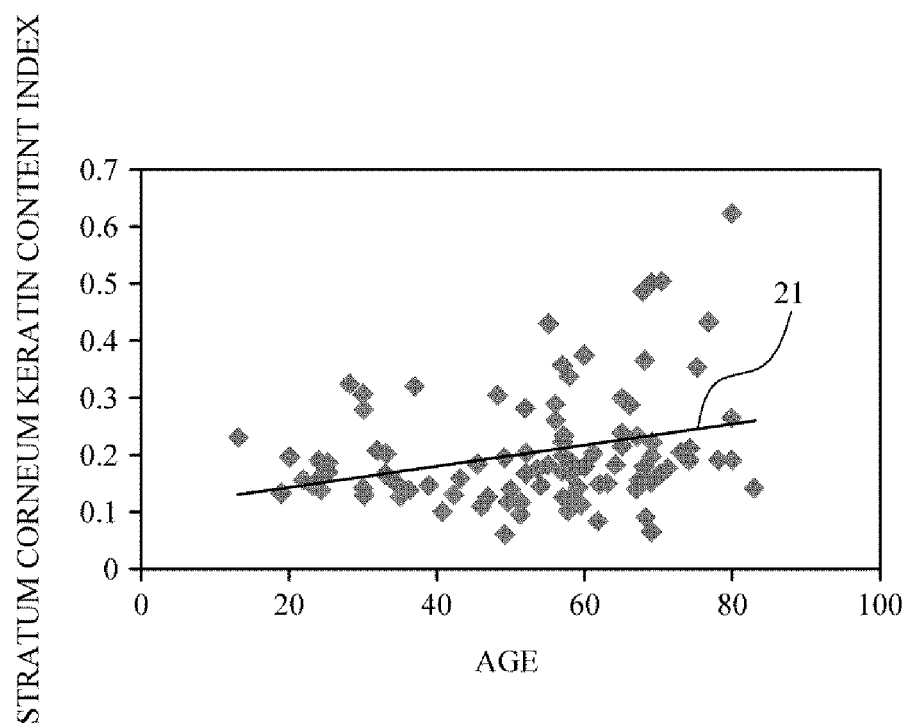
FIG. 2A is a graph illustrating a correlation between age and keratin content in stratum corneum.

FIG. 2A is a graph illustrating a correlation between age and keratin content in the stratum corneum. As shown by a trend line 21 illustrated in FIG. 2A, the keratin content in the stratum corneum increases with age. This pattern is closely associated with the phenomenon in which the stratum corneum becomes thickened with age, and indicates that the keratin content in the stratum corneum increases as the thickness of the stratum corneum increases. In this case, the trend line 21 indicates a positive correlation between age and an increase in keratin content in the stratum corneum, and it may be an example of the first estimation model.

Figure 2B:
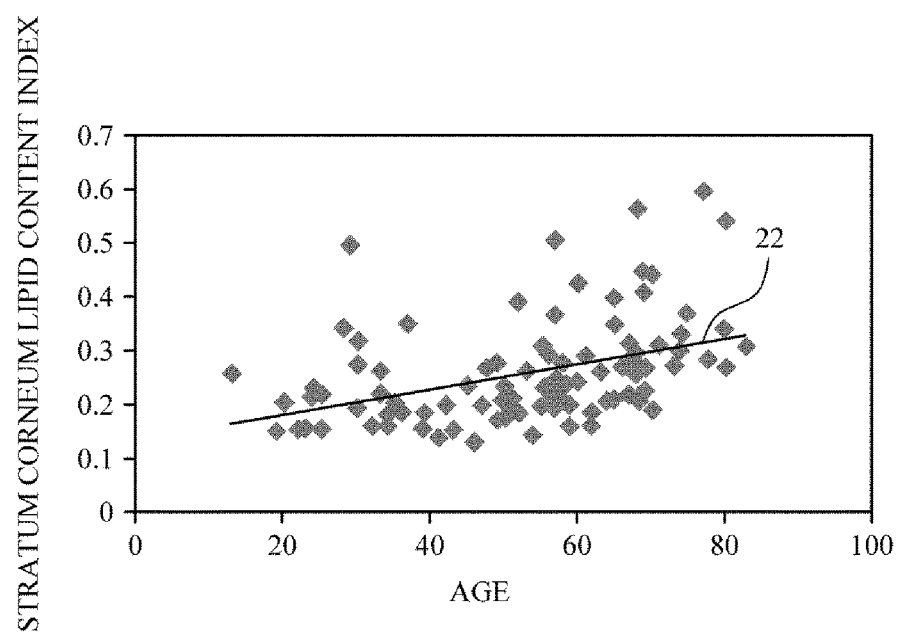
FIG. 2B is a graph illustrating a correlation between age and lipid content in stratum corneum.

FIG. 2B is a graph illustrating a correlation between age and lipid content in the stratum corneum.

As shown by a trend line 22 illustrated in FIG. 2B, the lipid content in the stratum corneum increases with age. This pattern is closely associated with the phenomenon in which the stratum corneum is thickened with age, and indicates that the lipid content in the stratum corneum increases as the thickness of the stratum corneum increases. In this case, the trend line 22 indicates a positive correlation between age and an increase in lipid content in the stratum corneum, and it may be an example of the second estimation model.

Figure 3A:
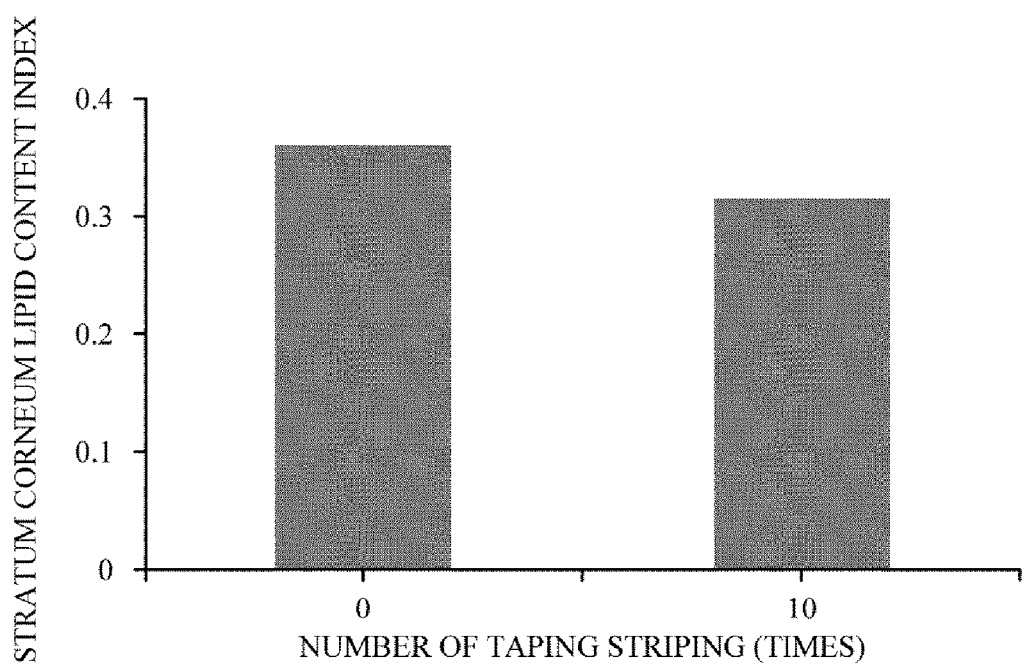
FIG. 3A is a graph showing a correlation between a degree of skin damage and lipid content in the stratum corneum.

FIG. 3A is a graph showing a correlation between a degree of skin damage and lipid content in the stratum corneum. Before the lipid content of the skin is measured, one or more tape stripping procedures are performed on the skin in order to cause damages to the skin and thereafter observe the effects of the tape stripping procedures.

As shown in FIG. 3A, the lipid content in the stratum corneum decreases with the number of times of tape striping on the skin, and in comparison to the case of no tape striping, an index of lipid content in the stratum corneum is decreased when the number of times of tape striping is 10, due to the damage of the skin by the tape striping. This pattern indicates that the lipid of the stratum corneum is damaged by the tape striping and falls off and hence the lipid content in the stratum corneum decreases. In other words, an increase in degree of skin damage and the lipid content in the stratum corneum are in a negative correlation.

Figure 3B:
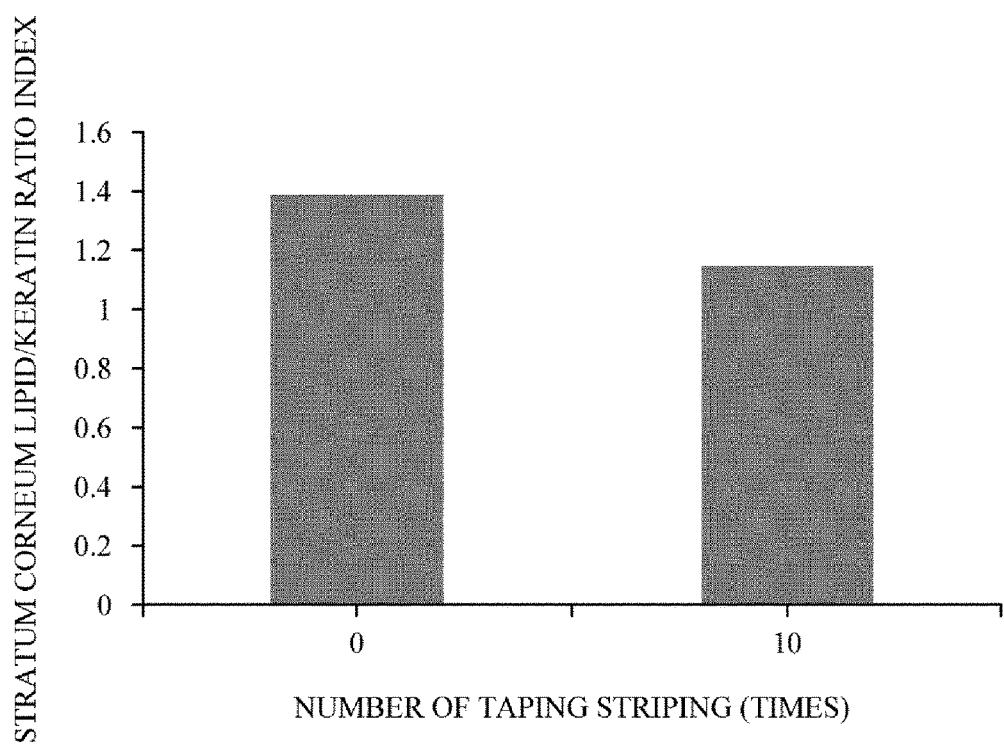
FIG. 3B is a graph illustrating a correlation between a degree of skin damage and a ratio between lipid and keratin in the stratum corneum.

FIG. 3B is a graph illustrating a correlation between a degree of skin damage and a ratio between lipid and keratin in the stratum corneum.

Referring to FIG. 3B, it is observed that the ratio between lipid and keratin decreases with the number of times of tape striping on the skin. This pattern shows that the lipid is damaged more than the keratin when the stratum corneum is damaged by tape striping. In other words, a degree of skin damage due to the tape striping and a variation in the ratio between the lipid and the keratin are in a negative correlation.

Figure 4:
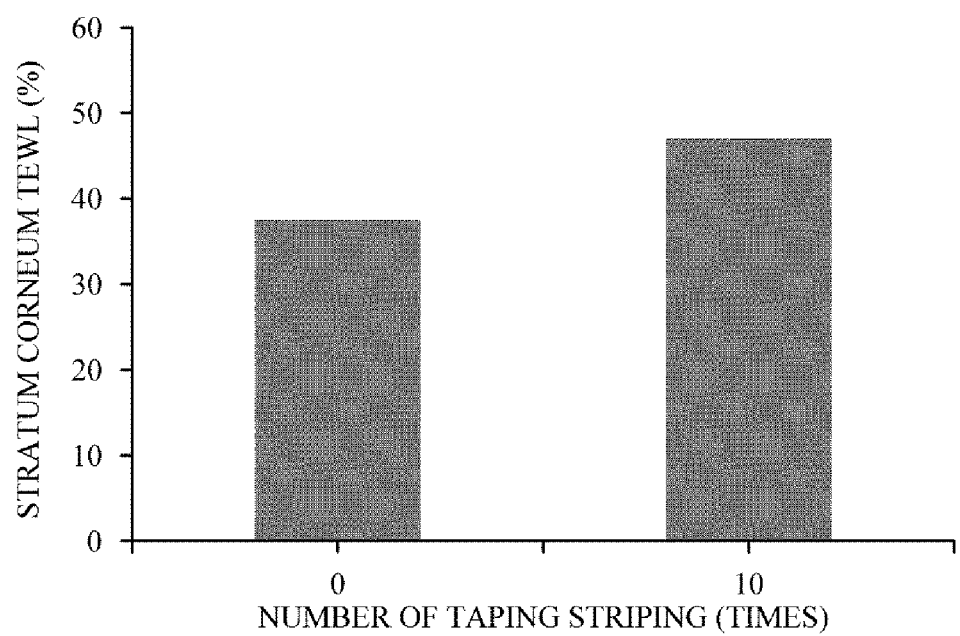
FIG. 4 is a graph showing a correlation between a degree of skin damage and stratum corneum transepidermal water loss (TEWL).

FIG. 4 is a graph showing a correlation between a degree of skin damage and stratum corneum TEWL. FIG. 4 shows a change in the stratum corneum TEWL due to tape striping on the skin.

Referring to FIG. 4, it is shown that, in comparison to the case of no tape striping, the stratum corneum TEWL increases when the number of times of tape striping on the skin is 10, and a degree of skin damage and the amount of stratum corneum TEWL are in a positive correlation.

Figure 5:
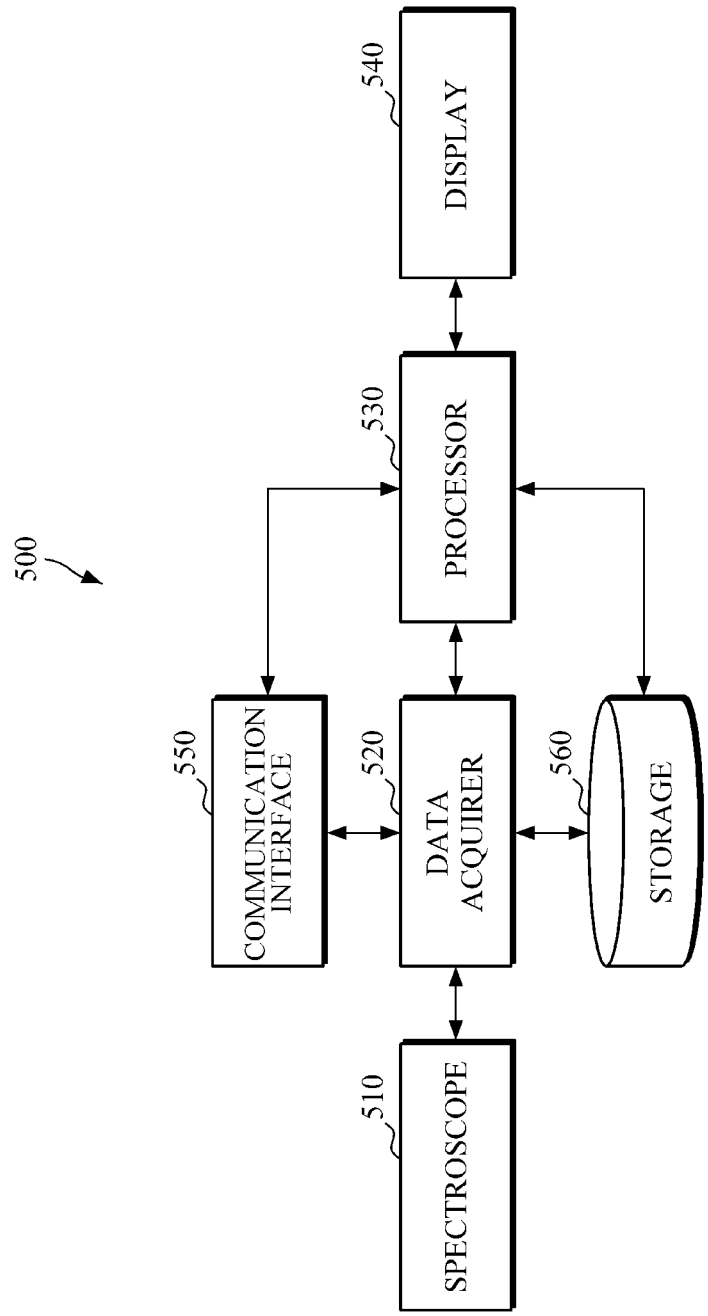
FIG. 5 is a block diagram illustrating an apparatus for estimating a skin condition according to another exemplary embodiment.

FIG. 5 is a block diagram illustrating an apparatus for estimating a skin condition according to another exemplary embodiment.

Referring to FIG. 5, the apparatus 500 includes a spectroscope 510, a data acquirer 520, a processor 530, a display 540, a communication interface 550, and a storage 560. In this exemplary embodiment, the data acquirer 520 and the processor 530 are configured to be the same as the data acquirer 110 and the processor 120 described with reference to FIG. 1, and the description, hereinafter, will be provided with focus on the configuration that has not been described above.

The spectroscope 510 may emit light to the user's skin, receive returning light scattered or reflected from the skin, and measure the skin spectrum by spectroscopy of the received light. To this end, the spectroscope 510 may include a light source including a light emitting diode (LED), a laser diode, or the like and a light detector including a photodiode, a photo transistor (PTr), a charged coupled device (CCD), or the like.

According to one exemplary embodiment, the spectroscope 510 may emit near-infrared light of a predetermined optical wavelength band into the user's skin and generate spectrum data of a specific area. For example, the spectroscope 510 may emit near-infrared light of a predetermined optical wavelength band (e.g., 1500 nm~1900 nm, FOB) and/or 2000 nm~2400 nm (combination band)) into the user's skin, and receive returning light to generate skin spectrum data. However, the aforementioned wavelength band is provided only for the purpose of example, and the present exemplary embodiment is not limited thereto.

The display 540 may display a result of skin condition estimation. For example, the display 510 may classify the results of skin condition estimation and display the classifications.

According to one exemplary embodiment, the display 540 may include a user interface (UI) configured to display the degree of skin aging, the degree of skin damage and the stratum corneum TEWL as individual items and display details of the skin condition estimation results, such as "good" "normal" "care needed".

The communication interface 550 may communicate with an external device in a wire/wireless manner.

According to one exemplary embodiment, the communication interface 550 may receive user's skin spectrum data from a separate spectroscope installed externally, or transmit the skin condition estimated by the processor 530 to an external device. For example, the communication interface 550 may receive an estimation result transmission request signal from the external device and transmit the estimated skin condition to the external device. In this case, the external device may be medical equipment which uses the estimated skin condition, a printer which prints out the result, or a display device which displays the estimated skin condition data. In addition, the external device may include, but not necessarily limited to, a digital TV, a desktop computer, a mobile phone, a smartphone, a tablet, a laptop, a PDA, a PMP, a navigation system, an MP3 player, a digital camera, a wearable device.

The communication interface 550 may include one or more modules which communicate via Bluetooth, Bluetooth low energy (BLE) communication, a near field communication unit, wireless local area network (WLAN) communication, ZigBee communication, infrared data association (IrDA) communication, Wi-Fi direct (WFD) communication, ultra-wideband (UWB) communication, Ant+ communication, Wi-Fi communication, 3G communication, 4G communication, 5G communication, etc.

The storage 560 may store the skin spectrum data obtained by the data acquirer 520 and the skin condition estimation result from the processor 530. Here, the storage 560 may include a flash memory, a hard disk, a micro type multimedia card, and a card type memory (e.g., SD or XD memory), a random access memory (RAM), a static random access memory (SRAM), a read only memory (ROM), an electrically erasable programmable read only memory (EEPROM), a programmable read only memory (PROM), a magnetic memory, a magnetic disk, an optical disk, and the like. In addition, the storage 560 may be an external storage medium, such as web storage, and a storage scheme is not particularly limited.

Figure 6:
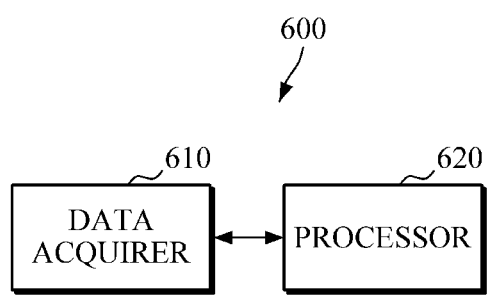
FIG. 6 is a block diagram illustrating an apparatus for estimating a skin condition according to another exemplary embodiment.

FIG. 6 is a block diagram illustrating an apparatus for estimating a skin condition according to another exemplary embodiment.

Referring to FIG. 6, the apparatus 600 includes a data acquirer 610 and a processor 620.

The data acquirer 610 may acquire skin spectrum data. Here, the skin spectrum data may be absorption spectrum data that is acquired by emitting near-infrared light of a predetermined optical wavelength band (e.g., 1500 nm~1900 nm, FOB) and/or 2000 nm~2400 nm (combination band)) into the user's skin.

According to one exemplary embodiment, the data acquirer 610 may be connected to an external spectroscopy device over a wired/wireless network, and acquire real-time skin spectrum data from the external spectroscopy device, or acquire skin spectrum data received from an external storage device. In addition, the data acquirer 610 may not be limited to the above, and may include a near-infrared light source of a specific optical wavelength band and a light detector and directly acquire the spectrum data.

The processor 620 may calculate the derivative of the acquired skin spectrum data. For example, the processor 620 may calculate the derivative of the acquired skin spectrum data using at least one of the Norris gap derivative algorithm and the Savitzky-Golay algorithm. However, the algorithms for calculating the derivative are not limited to the above examples. For example, the processor 620 may calculate the derivative of the acquired skin spectrum data using the Norris gap $2^{nd}$ order derivative algorithm, in which a differentiation interval is 1 (s=1).

The processor 620 may estimate a degree of skin damage from the amplitude of the derivative of the skin spectrum data. For example, the processor 620 may estimate the user's degree of skin damage using a degree-of-skin-damage estimation model. In this case, the degree-of-skin-damage estimation model may be an estimation model which defines the correlation between a degree of skin damage and the amplitude of the derivative of the skin spectrum data. The degree-of-skin-damage estimation model may be generated in advance based on changes in the amplitude of the derivative of the spectrum data according to a stepwise skin damage, wherein the changes are previously collected.

According to one exemplary embodiment, the processor 620 may estimate the degree of skin damage using the degree-of-skin-damage estimation model and the amplitude of the derivative of the skin spectrum data. In other words, the processor 620 may reference the degree-of-skin-damage estimation model to identify the degree of damage that corresponds to the amplitude of specific optical wavelength band in the $2^{nd}$ order derivative of the user's skin spectrum data and determine the identified degree of skin damage as the user's degree of skin damage, so that the degree of skin damage can be estimated. For example, the processor 620 may reference the degree-of-skin-damage estimation model and calculate the derivative of the user's skin spectrum data using at least one of the Norris gap derivative algorithm and the Savitzky-Golay algorithm. In other words, the processor 620 may calculate the derivative of the acquired skin spectrum data using the Norris gap $2^{nd}$ order derivative algorithm (s=1) and reference the degree-of-skin-damage estimation model to determine that the degree of skin damage which corresponds to the amplitude of the band of 1370~1380 nm in the calculated derivative is the user's degree of skin damage, so that the user's degree of skin damage can be estimated.

The processor 620 may estimate at least one of a degree of skin aging, a degree of skin damage, and the stratum corneum TEWL, and estimate the skin condition in a complex manner. For example, the processor 620 may estimate the degree of skin aging using the first estimation model and the second estimation model as described with reference to FIG. 1. In addition, the processor 620 may estimate the degree of skin damage using all of the third estimation model, the fourth estimation model, and the degree-of-skin-damage estimation model, and estimate the stratum corneum TEWL using the stratum-corneum-TEWL estimation model based on the above estimation result of degree of skin damage.

As such, the processor 620 may independently, successively, or concurrently estimate the degree of skin damage and the stratum corneum TEWL, and may estimate the overall skin condition by combining the estimation results of each item.

Figure 7:
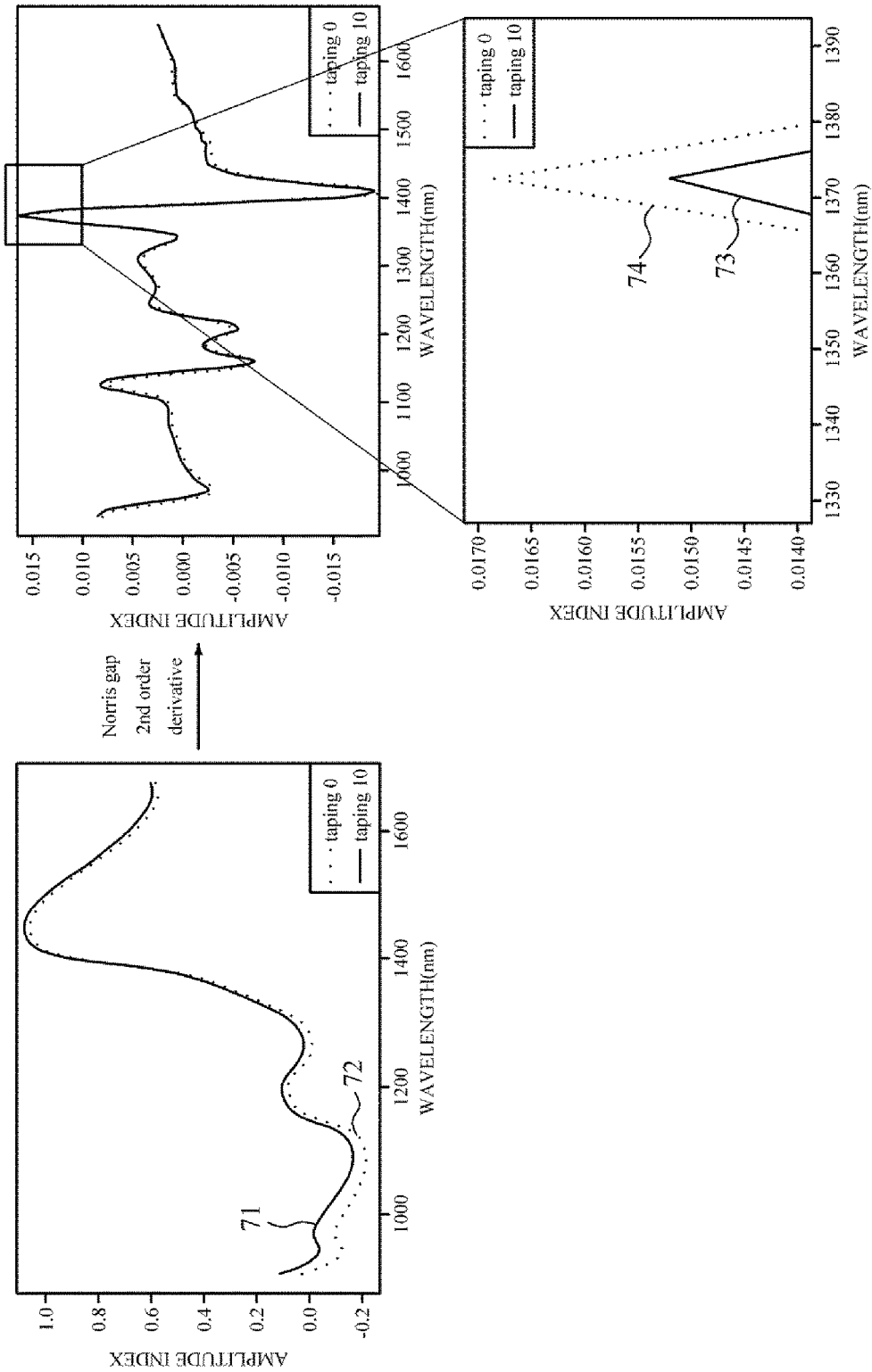
FIG. 7 illustrates graphs showing a correlation between a degree of skin damage and amplitude variation.

FIG. 7 illustrates graphs showing a correlation between a degree of skin damage and amplitude variation.

Referring to FIG. 7, it is shown that the graphs of skin spectrum data 71 and 72 associated with tape striping on the skin vary in shape. It is also shown that amplitudes of derivatives 73 and 74 of the skin spectrum data which are calculated using the Norris gap $2^{nd}$ derivative algorithm (s=1) vary with a degree of skin damage (e.g., the number of tape striping). That is, in an optical wavelength band of 1370 nm~1380 nm, the derivative 73 of the skin spectrum data 71 acquired in the case of no tape striping exhibits a smaller amplitude than the derivative 74 of the skin spectrum data 72 acquired in the case of 10 times of tape striping, and hence it appears that there is a correlation between a degree of skin damage and the amplitude of the derivative of the skin spectrum data.

FIG. 7 illustrates the correlation between a stepwise skin damage and the amplitude of an optical wavelength band of 1370 nm~1380 nm, but the amplitude is not limited to the amplitude of the wavelength range shown in FIG. 7.

Figure 8:
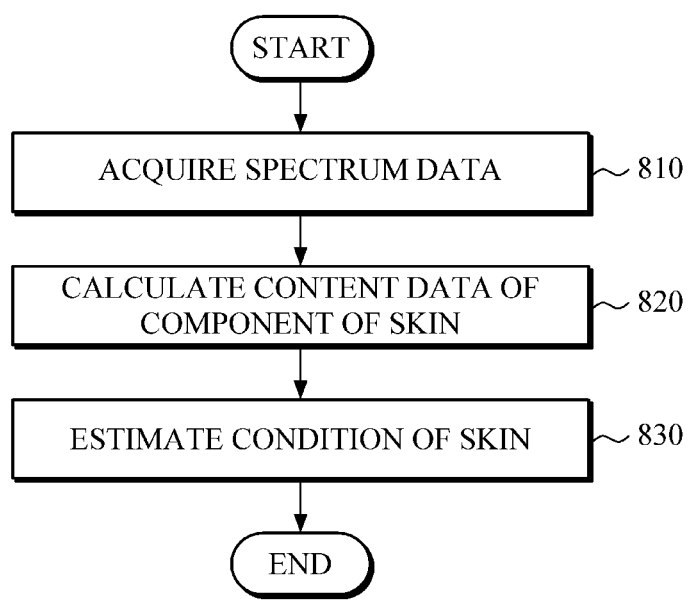
FIG. 8 is a flowchart illustrating a method for estimating a skin condition according to an exemplary embodiment.

FIG. 8 is a flowchart illustrating a method for estimating a skin condition according to an exemplary embodiment. The method shown in FIG. 8 is an example of a skin condition estimation method which is performed by the apparatus 100 for estimating a skin condition of FIG. 1.

Referring to FIGS. 1 and 8, the apparatus 100 acquires spectrum data in operation 810. For example, the apparatus 100 may be connected to an external device including a near-infrared light source and a spectroscope in a wired/wireless manner and acquire spectrum data of a specific optical wavelength band (e.g., 1500 nm~1900 nm: FOB) and/or 2000 nm~2400 nm (combination band).

The apparatus 100 calculates the content data of a component in the skin from the acquired skin spectrum data in operation 820.

According to one exemplary embodiment, the apparatus 100 may calculate the content data of a component in the skin by comparing the extracted individual component spectrum data with pure spectrum data of the pertinent component. Here, the pure spectrum data may refer to spectrum data of a specific amount of pure component, for example, spectrum data of pure keratin (hereinafter, referred to as pure keratin spectrum data) or spectrum data of pure lipids (hereinafter, referred to as pure lipid spectrum data), and may be data that is collected in advance and stored. The pure spectrum data may be also referred to as reference spectrum data.

For example, the apparatus 100 may compare the keratin spectrum data extracted from the skin spectrum data with the pure keratin spectrum data to calculate keratin content data, or may compare the lipid spectrum data extracted from the skin spectrum data with the pure lipid spectrum data to calculate lipid content data.

The apparatus 100 estimates a skin condition based on the calculated content data of component in operation 830. Here, the skin condition may include a degree of skin aging and a degree of skin damage.

According to one exemplary embodiment, the apparatus 100 may estimate the skin condition from the content data of skin component using at least one of a skin condition estimation model and a stratum-corneum-TEWL estimation model. Here, the skin condition estimation model may include the first estimation model which defines the correlation between a degree of skin aging and the keratin content data, the second estimation model which defines the correlation between a degree of skin aging and the lipid content data, the third estimation model which defines the correlation between a degree of skin damage and the lipid content data, and the fourth estimation model which defines the correlation between a degree of skin damage and a ratio between lipid and keratin.

According to one exemplary embodiment, the apparatus 100 may estimate the user's degree of skin aging from the content data of skin component using at least one of the first estimation model and the second estimation model.

For example, the apparatus 100 may reference the first estimation model to identify the age that corresponds to the keratin content in the stratum corneum of the user's skin and determine the identified age as the user's skin age, so that the degree of skin aging can be estimated.

In another example, the apparatus 100 may reference the second estimation model to identify the age that corresponds to the lipid content in the stratum corneum of the user's skin and determine the identified age as the user's skin age, so that the user's degree of skin aging can be estimated.

In still another example, the apparatus 100 may estimate a degree of skin aging using both the first estimation model and the second estimation model. Specifically, the apparatus 100 may estimate the user's degree of skin aging by combining a first degree of skin aging estimated using the calculated keratin content data and the first estimation model and a second degree of skin aging estimated using the calculated lipid content data and the second estimation model. For example, the apparatus 100 may calculate an average value of the first degree of skin aging and the second degree of skin aging, and determine the average value as the user's degree of skin aging. In another example, the apparatus 100 may give different weights to the first degree of skin aging and the second degree of skin aging in combining the first degree and the second degree.

According to another exemplary embodiment, the apparatus 100 may estimate the user's degree of skin damage from the content data of skin component using at least one of the third estimation model and the fourth estimation model.

For example, the apparatus 100 may reference the third estimation model to identify a degree of damage that corresponds to the lipid content in the stratum corneum of the user's skin and determine the identified degree as the user's degree of skin damage, so that the user's degree of skin damage can be estimated.

In another example, the apparatus 100 may reference the fourth estimation model to identify a degree of damage that corresponds to the ratio between lipid and keratin in the stratum corneum of the user's skin and determine the identified degree as the user's degree of skin damage, so that the user's degree of skin damage can be estimated.

In still another example, the apparatus may estimate the degree of skin damage using both the third estimation model and the fourth estimation model. For example, the apparatus 100 may estimate the user's degree of skin damage more accurately by combining the degree of skin damage which is estimated using the calculated lipid content data and the third estimation model and the degree of skin damage which is estimated using the ratio between lipid and keratin and the fourth estimation model.

According to another exemplary embodiment, the apparatus 100 may estimate stratum corneum TEWL from the estimated skin condition using a stratum-corneum-TEWL estimation model. Here, the stratum-corneum-TEWL estimation model may be an estimation model which defines the correlation between a degree of skin damage and the stratum corneum TEWL. For example, the apparatus 100 may reference the stratum-corneum-TEWL estimation model to identify stratum corneum TEWL that corresponds to the user's degree of skin damage and determine the identified stratum corneum TEWL as the user's stratum corneum TEWL.

Figure 9:
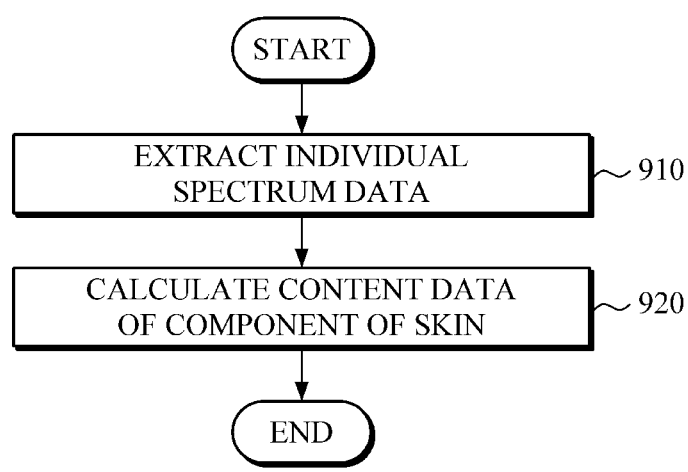
FIG. 9 is a flowchart illustrating operation 820 of FIG. 8 in detail.

FIG. 9 is a flowchart illustrating operation 820 of FIG. 8 in detail. The flowchart shown in FIG. 9 may be one example of a method for estimating a skin condition that is performed by the apparatus 500 of FIG. 5.

Referring to FIGS. 5 and 9, the apparatus 500 extracts individual component spectrum data from the acquired skin spectrum data in operation 910.

Here, the individual component spectrum data may refer to spectrum data of each component in the skin. For example, the skin components may include water, keratin, lipids, collagen, and the like. Individual component spectrum data, such as a water spectrum, a keratin spectrum, a lipid spectrum, and a collagen spectrum, may be extracted from the acquired skin spectrum data.

After extracting the individual component spectrum data, the apparatus 500 calculates the content data of a component in the skin in operation 920.

According to one exemplary embodiment, the apparatus 500 may calculate the content data of a component in the skin by comparing the extracted individual component spectrum data with pure spectrum data of the pertinent component. For example, the apparatus 500 may compare the keratin spectrum data extracted from the skin spectrum data with the pure keratin spectrum data to calculate keratin content data, or may compare the lipid spectrum data extracted from the skin spectrum data with the pure lipid spectrum data to calculate lipid content data.

Figure 10:
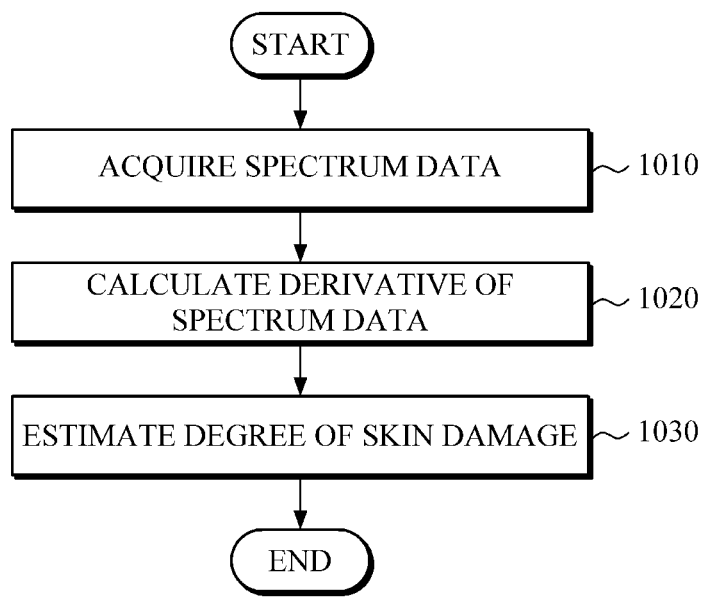
FIG. 10 is a flowchart illustrating method for estimating a skin condition according to another exemplary embodiment.

FIG. 10 is a flowchart illustrating a method for estimating a skin condition according to another exemplary embodiment. The method shown in FIG. 10 may be one example of a method for estimating a skin condition which is performed by the apparatus of FIG. 6.

Referring to FIGS. 6 and 10, the apparatus 600 acquires spectrum data in operation 1010. For example, the apparatus 600 may be connected to an external device including a near-infrared light source and a spectroscope in a wired/wireless manner and acquire spectrum data of a specific optical wavelength band.

Once the apparatus 600 has acquired the spectrum data, the apparatus 600 calculates a derivative of the acquired skin spectrum data in operation 1020. For example, the apparatus 600 may calculate the derivative of the acquired skin spectrum data using at least one of the Norris gap derivative algorithm and the Savitzky-Golay algorithm. However, the algorithms for calculating the derivative are not limited to the above examples.

The apparatus 600 extracts a degree of skin damage from the amplitude of the derivative of the skin spectrum data in operation 1030. For example, the apparatus 600 may estimate the user's degree of skin damage using a degree-of-skin-damage estimation model. Here, the degree-of-skin-damage estimation model may be an estimation model which defines the correlation between a degree of skin damage and the amplitude of the derivative of the skin spectrum data. The degree-of-skin-damage estimation model may be generated in advance based on changes in the amplitude of the derivative of the spectrum data according to a stepwise skin damage, wherein the changes are previously collected. For example, the apparatus 600 may reference the degree-of-skin-damage estimation model and calculate the derivative of the user's skin spectrum data using at least one of the Norris gap derivative algorithm and the Savitzky-Golay algorithm. In other words, the apparatus 600 may calculate the derivative of the acquired skin spectrum data using the Norris gap $2^{nd}$ order derivative algorithm (s=1) and reference the degree-of-skin-damage estimation model to determine that the degree of skin damage which corresponds to the amplitude of the band of 1370~1380 nm in the calculated derivative is the user's degree of skin damage, so that the user's degree of skin damage can be estimated.

Figure 11:
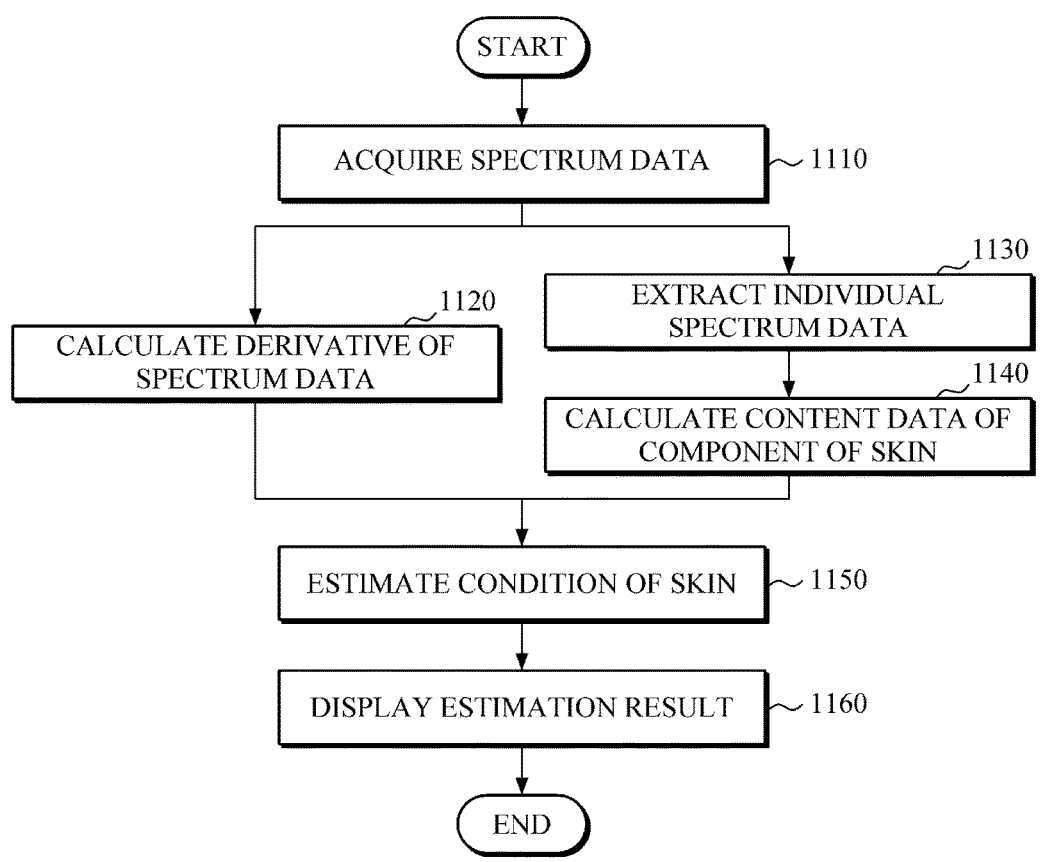
FIG. 11 is a flowchart illustrating a method for estimating a skin condition according to another exemplary embodiment.

FIG. 11 is a flowchart illustrating a method for estimating a skin condition according to another exemplary embodiment. The method shown in FIG. 11 may be one example of a method for estimating a skin condition which is performed by the apparatus 600 of FIG. 6.

Referring to FIGS. 6 and 11, the apparatus 600 acquires skin spectrum data in operation 1110.

Once the apparatus 600 has acquired the skin spectrum data, the apparatus 600 calculates a derivative of the acquired skin spectrum data in operation 1120. For example, the apparatus 600 may calculate the derivative of the acquired skin spectrum data using at least one of the Norris gap derivative algorithm and the Savitzky-Golay algorithm. However, the algorithms for calculating the derivative are not limited to the above examples.

Meanwhile, the apparatus 600 extracts individual component spectrum data from the acquired skin spectrum data in operation 1130. For example, the apparatus 600 may extract the individual component spectrum data from the acquired skin spectrum data using a regression analysis algorithm.

After extracting the individual component spectrum data from the spectrum data, the apparatus 600 calculates the content data of a component in the skin by comparing the extracted individual component spectrum data with a pure spectrum of a pertinent component in the skin in operation 1140. Although FIG. 11 illustrates that the calculation of the $2^{nd}$ order derivative of the acquired spectrum data in operation 1120, the extraction of the individual component spectrum data in operation 1130, and the calculation of the content data of a component in the skin in operation 1140 are performed in parallel, the exemplary embodiment is not limited thereto, such that these operations may be independently or successively performed.

The apparatus 600 estimates the user's skin condition using the calculated derivative of the spectrum data and the content data of the component in the skin in operation 1150. For example, the apparatus 600 may estimate the user's degree of skin aging using both the first and second estimation models, and the apparatus 500 may estimate the user's degree of skin damage from the calculated $2^{nd}$ order derivative of the spectrum data using the degree-of-skin-damage estimation model.

As such, the apparatus 600 may analyze the amplitude of the derivative using the acquired skin spectrum data, extract the individual component spectrum data, calculate the content data of the component in the skin, and estimate the degree of skin aging and the degree of skin damage, thereby estimating the overall skin condition.

The apparatus 600 displays the estimation result of the degree of skin damage and the degree of skin aging in operation 1160. For example, the apparatus 600 may display the degree of skin aging and the degree of skin damage as individual items and display details of the skin condition estimation results, such as "good" "normal" "care needed". The apparatus 600 may store a range of the degree of skin aging and another range of the degree of skin damage that correspond to the skin condition estimation result of "good."

While not restricted thereto, an exemplary embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for estimating a skin condition, the apparatus comprising:
a data acquirer configured to acquire an optical absorption spectrum of a skin of a user;

a storage configured to store a regression analysis algorithm, and reference data indicating a relation between a degree of skin damage and a ratio of a lipid content to a keratin content; and a processor configured to extract a keratin spectrum and a lipid spectrum from the optical absorption spectrum based on the regression analysis algorithm, and determine a skin condition of the user based on comparison between the keratin spectrum and the lipid spectrum extracted from the optical absorption spectrum, and the reference data indicating the relation between the degree of skin damage and the ratio of the lipid content to the keratin content.

2. The apparatus of claim 1, wherein the regression analysis algorithm corresponds to a least square regression (LSR) algorithm, a partial least square regression (PLSR) algorithm, a principal component regression (PCR) algorithm, or a multivariate regression algorithm.

3. The apparatus of claim 1, wherein the processor is further configured to calculate a derivative of the optical absorption spectrum by using a Savitzky-Golay algorithm, and determine the skin condition based on comparison between amplitudes of the derivative at wavelength bands that respectively correspond to the keratin content and the lipid content, and the reference data stored in the storage.

4. The apparatus of claim 1, wherein the processor is further configured to calculate a derivative of the optical absorption spectrum by using a Norris gap derivative algorithm, and determine the skin condition based on a comparison between amplitudes of the derivative at wavelength bands that respectively correspond to the keratin content and the lipid content, and the reference data stored in the storage.

5. The apparatus of claim 1, wherein the processor is further configured to determine stratum corneum transepidermal water (TEWL) from the optical absorption spectrum based on a stratum-corneum-TEWL estimation model that is generated based on a regression algorithm using the degree of skin damage and the stratum corneum TEWL as an independent variable and a dependent variable, respectively.

6. The apparatus of claim 1, further comprising:
a display configured to display information of the skin condition; and
a communication interface configured to transmit the information of the skin condition to an external device.

7. The apparatus of claim 1, further comprising a spectroscope configured to emit near-infrared light into the skin and generate the optical absorption spectrum through spectroscopy of the near-infrared light reflected or scattered from the skin.

8. A method for estimating a skin condition, the method comprising:

storing a regression analysis algorithm, and reference data indicating a relation between a degree of skin damage and a ratio of a lipid content to a keratin content;

acquiring an optical absorption spectrum of a skin;

extracting a keratin spectrum and a lipid spectrum from the optical absorption spectrum based on the regression analysis algorithm; and determining a skin condition based on comparison between the keratin spectrum and the lipid spectrum extracted from the optical absorption spectrum, and the reference data indicating the relation between the degree of skin damage and the ratio of the lipid content to the keratin content.

9. The method of claim 8, wherein the regression analysis algorithm corresponds to a least square regression (LSR) algorithm, a partial least square regression (PLSR) algorithm, a principal component regression (PCR) algorithm, or a multivariate regression algorithm.

10. The method of claim 8, wherein the determining the skin condition comprises estimating stratum corneum transepidermal water (TEWL) from the optical absorption spectrum based on a stratum-corneum-TEWL estimation model that is generated based on a regression algorithm using the degree of skin damage and the stratum corneum TEWL as an independent variable and a dependent variable, respectively.

11. The method of claim 8, further comprising displaying information of the skin condition.

12. The method of claim 8, wherein the acquiring the optical absorption spectrum comprises emitting near-infrared light into the skin and generating the optical absorption spectrum through spectroscopy of the near-infrared light reflected or scattered from the skin.

13. An apparatus for estimating a skin condition, the apparatus comprising:

a data acquirer configured to acquire an optical absorption spectrum of a skin of a user;

a storage configured to store a Norris gap derivative or a Savitzky-Golay algorithm, and store reference data indicating a relation between a degree of skin damage and a second order derivative of the optical absorption spectrum; and a processor configured to calculate a derivative of the absorption spectrum using the Norris gap derivative algorithm or the Savitzky-Golay algorithm, and determine a skin condition of the user based on comparison between an amplitude of the calculated derivative of the optical absorption spectrum and the reference data indicating the relation between the degree of skin damage and the second order derivative of the optical absorption spectrum.

* * * * *